(12) United States Patent
Narayanan et al.

(10) Patent No.: US 6,767,548 B2
(45) Date of Patent: Jul. 27, 2004

(54) GEL INHIBITED LIQUID CARRIER FOR A BIOCIDE CONTAINING A CARBODIIMIDE AND AN EMULSIFIER MIXTURE

(75) Inventors: Kolazi S. Narayanan, Wayne, NJ (US); Domingo Jon, New York, NY (US); George B. Beestman, Madison, WI (US)

(73) Assignee: ISP Investments Inc., Wilmington, DE (US)

(*) Notice: Subject to any disclaimer, the term of this patent is extended or adjusted under 35 U.S.C. 154(b) by 24 days.

(21) Appl. No.: 10/077,612

(22) Filed: Feb. 15, 2002

(65) Prior Publication Data
US 2003/0165554 A1 Sep. 4, 2003

(51) Int. Cl.[7] ............................................. A01N 25/04
(52) U.S. Cl. .................... 424/405; 424/421; 424/641; 424/683; 424/684; 424/688; 424/691; 424/692; 514/245; 514/631; 514/637
(58) Field of Search ................... 514/245, 631, 514/637; 424/405, 421, 683, 684, 688, 691, 692, 641, 409

(56) References Cited

FOREIGN PATENT DOCUMENTS

WO      99/18782    *   4/1999

* cited by examiner

Primary Examiner—Neil S. Levy
(74) Attorney, Agent, or Firm—Marilyn J. Maue; William J. Davis; Walter Katz

(57) ABSTRACT

This invention relates to a biocidal composition resistant to the formation of a gel and to the method for stabilizing a concentrate containing, in addition to the biocide, a carbodiimide, a lipophilic/hydrophilic emulsifier mixture having a HLB of 6 to 20 and optionally an oil and/or an alkoxylated ester of a polyhydroxylated compound, by adding to the concentrate an effective anti-gelling amount of an anti-gelling agent selected from the group of an inorganic oxide, a epoxidized naturally occurring or synthetic vegetable oil and an epoxylated ester of a saturated or unsaturated $C_6$ to $C_{18}$ aliphatic acid optionally containing hydroxy substitution and mixtures of the foregoing anti-gelling agents.

19 Claims, No Drawings

GEL INHIBITED LIQUID CARRIER FOR A BIOCIDE CONTAINING A CARBODIIMIDE AND AN EMULSIFIER MIXTURE

BACKGROUND OF THE INVENTION

Liquid carrier compositions for herbicides, insecticides, fungicides and other biocidally active compounds which contain an emulsifier mixture of an oil and an alkoxylated ester of a polyhydroxylated hydrocarbon and a carbodiimide or polymer thereof are useful agrochemical solutions and additionally have several other non-agrochemical uses including diluents for forming oil-in-water (ON) or water-in-oil (W/O) microemulsions for cleaning and disinfecting formulations, pesticidal sprays or dips for treating livestock and domesticated pets, etc. The concentrates also find use as additives to existing commercial formulations for the stabilization of many active compounds. Such concentrates are particularly useful for preventing or minimizing the degradation of water labile biocidally active aza compounds. Typically, a formulation containing aza compounds in a concentrate is disclosed in our co-pending U.S. patent application Ser. No. 09/169,697. This anhydrous concentrate additionally contains a carbodiimide, a $C_8$-$_{18}$ alkyl lactam and a lipophilic/hydrophilic emulsifier mixture. The compositions disclosed in this patent are suitably employed for the present treatment preventing gel formation and are incorporated herein by reference.

While several prior concentrate carriers containing a carbodiimide and an emulsifier mixture are highly effective in producing microemulsions and initially sprayable liquids which are stabilized against decomposition of the active agent, it has been found that in many cases the active carrier itself is subject to gel formation during subsequent handling or storage, particularly during storage at elevated temperatures, or when higher concentrations of the alkoxylated esters or carbodiimide, water scavenging agent, are present in the concentrate. Since, for certain applications including pump and aerosol sprays, crop spraying and animal dips, gel formation is undesirable, extensive research has been directed to extending the shelf life of such concentrates or solutions to accommodate delayed use of at least a portion of the liquid concentrate.

Accordingly it is an object of this invention to overcome the above problem by providing a diluent solution or concentrate which does not undergo thickening or gelling for a period up to 6 months or more while retaining stability of the active component and other desirable formulation characteristics.

Another object is to provide a pesticidal microemulsion suitable for spray or dip administration to crops, livestock and pets.

Another object is to provide an effective and economical gel inhibited formulation containing a stabilized biocidally active compound in aqueous solution which has extended shelf life at both ambient and elevated temperatures.

These and other objects of the invention will become apparent from the following description and disclosure.

SUMMARY OF THE INVENTION

In accordance with this invention there is provided a stable anhydrous, gel free, liquid concentrate having a Brookfield viscosity less than 1,000 cps essentially containing, as the concentrate, (i) an active biocidal component, (ii) a carbodiimide and (iii) a lipophilic/hydrophilic emulsifier mixture having an HLB of 6–20, to which is added between about 0.5 and about 30 wt. %, based on total concentrate composition, of an anti-gelling agent which is an inorganic oxide of an alkaline earth element, an epoxidized vegetable oil or an epoxidized ester of a saturated or unsaturated $C_6$ to $C_{18}$ aliphatic acid optionally containing hydroxy substitution and mixtures of the foregoing anti-gelling agents. The concentrate may additionally contain up to 40 wt. % of an oil solvent to solubilize certain anti-gelling agents or active components which are not readily assimilated in the concentrate system.

DETAILED DESCRIPTION OF THE INVENTION

The liquid concentrates of this invention comprise formulations containing between about 0.05 and about 25 wt. % of a biocidally active, hydrolytically unstable, component which includes insecticidal, fungicidal, pesticidal and herbicidal compounds which include the class of aza compounds containing the structure

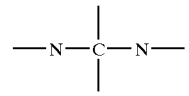

where one or both of the free
carbon bonds can form a double bond with nitrogen or is singly or doubly bonded to another atom or group. Suitable examples of such active biocides include an imine such N-methyl bis(2,4-xylyl iminomethyl amine), e.g. AMITRAZ; n-cyclopropyl-1,3,5-triazine-2,4,6-triamine [Cyromazine]; chlorsulfuron; sulfometuron; metsulfuron-methyl; thifensulfuron and the like, of which AMITRAZ is preferred. The aza compounds are those normally employed to treat livestock, such as sheep or cattle, feral animals and household pets. Other suitable aza compounds are those disclosed in my co-pending U.S. patent application Ser. No. 09/169,697 and U.S. Pat. No. 5,731,264, incorporated herein by reference.

Instant concentrate may contain between about 5 and about 40 wt. % organic solvent for water soluble or water insoluble active components. Such organic solvents can be water soluble or water insoluble and include those conventionally employed such as ethanol, cyclohexane, N-alkyl lactam, cyclic lactone and $C_8$ to $C_{12}$ alkyl pyrrolidone and mixtures thereof; N-octyl pyrrolidone being preferred.

The present concentrate composition essentially contains between about 2 and about 20 wt. %, preferably 5–15 wt. %, of a carbodiimide having water scavenging and dehydrating properties. The carbodiimide can be in monomeric or polymeric form, or a mixture thereof. Suitable carbodiimide scavenging agents are those which are terminally hindered by a polymeric or non-polymeric substituent on a terminal imide nitrogen. The terminal substituent is a non-functional linear, branched, cycloaliphatic, heterocyclic or an aromatic radical and can be defined by the following formulae A and B:

R—N=C=N—R'     A.

wherein R and R' are each individually aliphatic, aromatic, alkylaromatic carbocyclic or heterocyclic radicals. At least one of R and R' is most desirably an alkyl substituted phenyl group, such as the 2,6-diisopropyl phenyl group and

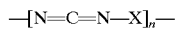

wherein n has a positive value up to 100; preferably a value of 10–20, and X is an alkyl substituted phenylene group, for example 2,4,6-tri isopropyl phenyl. Of these, the carbodiimides having a terminal nitrogen atom substituted with alkylphenyl, alkoxyalkylphenyl, sulfonate, sulfonamide, imido, imidoester, and sulfonyl urea groups are most effective. Particularly preferred scavengers are bis(tetraisopropyl phenyl) carbodiimide, bis(hydroxyphenyl) carbodiimide and bis(di-isopropylphenyl carbodiimide, e.g. (STABAXOL I) supplied by Rhein Chemie).

The carbodiimide component in the concentrate is polyfunctional in that it acts not only as a water scavenger but also becomes part of a micelle which envelops water insoluble biocides so that, upon subsequent dilution of the concentrate with water, a homogeneous liquid emulsion, suitable for spray application, can be obtained. While the water scavenging function of the carbodiimide can be replaced, in whole or in part, by a less costly inorganic water scavenger, e.g. an inorganic oxide, or other organic water scavenger sufficient carbodiimide must be retained in the concentrate to assure micellar containment of the water insoluble active component in the subsequent formation of a homogeneous emulsion suitable for plant spraying or immersion or spraying of animals. Further the carbodiimide which is present in the micellar composition protects the enveloped active component from water thus preventing hydrolytic decomposition.

The emulsifier portion of the present liquid composition comprises between about 25 and about 85 wt. %, preferably between about 40 and 60 wt. %, of the composition and is a mixture of lipophilic and hydrophilic surfactants having a HLB of from 6 to 20, preferably 9–11.

In general, the lipophilic character of the present emulsifiers is enhanced by a lower number of alkoxy groups in the compound or the higher molecular weight of an alkyl group in the N-alkyl lactam or ester; whereas hydrophilic character of the emulsifier is enhanced by a higher number of alkoxy groups, e.g. >30, or lower alkyl lactams or esters. Thus, if desired the lipophilic/hydrophilic emulsifier mixture can contain mixtures of the same oil with varying degrees of alkoxy substitution, mixtures of lower and higher alkyl lactams, etc. Preferably, the lipophilic/hydrophilic mixture contains emulsifiers which may have from 8 to 60 $C_2$ to $C_3$ alkoxy groups and the most preferred mixture has an acid number of less than 5.

Representative examples of suitable lipophilic emulsifiers include alkoxylated mineral oils, vegetable oils, triglycerides such as castor oil, soybean oil, linseed oil, rapeseed oil, $C_6$ to $C_{18}$ alkyl lactams and mixtures thereof. Suitable lipophilic oils are those having from 2 to 30 units of $C_2$ to $C_3$ alkoxy units. Of these, ethoxylated castor oils containing 12–40 ethoxy units, available as ALKAMULS® EL or CO 15, supplied by Rhone Poulenc, or ETHOX CO 16 supplied by Ethox Chemicals are preferred.

Representative examples of the hydrophilic emulsifiers include hydroxylated, alkoxylated esters derived from condensates of carboxylic acids such as sorbic-, oleic-, stearic- and palmitic-acids and generally contain 10 to 80, more desirably 15 to 60, alkylene groups. These hydrophilic esters also contain from 8 to 60 alkoxy units as in alkoxylated sorbitan monooleate and alkoxylated castor oil. Other hydrophilic emulsifiers, such as anionic alkyl phosphates and sulfonates can also be used as well as alkoxylated reduced sugars, e.g. saturated alkoxylated sorbitan, etc. Mixtures of these or optionally at least one of these in combinations with the above acid condensate esters may form the hydrophilic portion of the emulsifier mixture. To obtain a desirable HLB, between about 20 and about 80 wt. % of an alkoxylated lipophilic oil and between about 80 and about 20 wt. % of a hydrophilic hydroxylated, alkoxylated ester is recommended. Of the hydrophilic emulsifiers ethoxylated sorbitan mono-, di- and/or tri-oleate, e.g. (ALKAMULS® PSMO 20, Rhone Poulenc) and $C_8$ to $C_{12}$ alkyl phosphates are preferred.

The liquid concentrate compositions can also contain additional additives and inert excipients to satisfy the needs of the consumer or the requirements of a certain active component in emulsion or solution. The aza pesticidal concentrate compositions disclosed in co-pending U.S. patent application Ser. No. 09/169,697 and U.S. Pat. No. 5,731,264 and incorporated herein by reference, are most suitably employed in the present invention involving the anti-gelling additive.

The present dip and spray concentrate formulations at the above described concentrations are inhibited against gel formation during storage at both ambient and elevated temperatures by the addition of the present anti-gellants which include inorganic oxides and epoxylated oil and esters.

For the purposes of this disclosure, the terms "epoxy" and "epoxidized" compounds includes those which, in addition to the epoxy moiety, further contain a 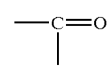 group as in glycidyl compounds.

The epoxylated anti-gelling agents of this invention include saturated and alkyleneically unsaturated compounds, both of which may contain one or more hydroxy groups. Where unsaturated or hydroxy substituted epoxides are employed as the anti-gellant, the epoxy or glycidyl moiety portion of the compound represents at least 5%, preferably 10%, of the double bond and/or the hydroxy content in the molecule.

To obtain anti-gelling properties in the above liquid concentrates or solutions, between about 0.5 and about 30 wt. %, preferably between about 1 and about 10 wt. %, of the anti-gellant is added and uniformly mixed therein. Between about 1.3 and about 6 wt. % anti-gellant, based on total composition, is most desirable.

Representative examples of the present anti-gelling agent include the oxides of Ca, Mg, Zn and Al, e.g. alumina; epoxy derivatives of linseed, safflower, soybean, corn, cottonseed, rapeseed or peanut oil; epoxy esters of saturated or unsaturated $C_6$ to $C_{18}$ aliphatic acids and their hydroxy-containing derivatives such as epoxidized (glyceryl oleate, epoxidized dodecyl linolenate, epoxidized 9,10-dihydroxy octyl stearate, glycidyl butylpalmitate, glycidyl laurate and the like) and mixtures of anti-gelling agents. Of the above, calcium oxide and epoxidized linseed or soybean oil are most preferred.

The present composition can be prepared by simply contacting the above mixture of concentrate components and the anti-gelling agent, with constant agitation at ambient temperature up to about 70° C. until a homogeneous composition is obtained. Alternatively, the concentrate components can be premixed and the anti-gelling agent added subsequently or, as a further alternate, the concentrate components, excluding the active biocide, can be mixed for subsequent addition of the active component.

A typical gel-resistant biocidally active concentrate or solution of this invention contains:

(a) between about 0.05 and about 25 wt. % of the biocidally active component;

(b) between about 0 and about 40 wt. % of an organic oil;
(c) between about 2 and about 20 wt. % of the terminally hindered carbodiimide
(d) between about 10 and about 80 wt. % of the lipophilic/hydrophilic emulsifier mixture having a HLB of 6–20 and
(e) between about 0.5 and about 20 wt. %, based on (a) through (d) of an anti-gelling agent selecterd from the group consisting essentially of an inorganic oxide, an epoxidized ester of a naturally occurring or synthetic vegetable oil and an epoxidized ester of a saturated or unsaturated $C_6$ to $C_{18}$ aliphatic acid optionally containing hydroxy substitution and mixtures of said anti-gelling agents.

Having generally described the invention, reference is now had to the following examples which set forth comparisons and preferred embodiments but which are not to be construed as limiting to the scope of the invention as defined in the appended claims.

EXAMPLE 1
Concentrate Carrier Composition for Biocide

The following compositions (100 g. each) were prepared by mixing in a glass bottle at room temperature.

| Component | Wt. % Sample A | Wt. % Sample B |
|---|---|---|
| N-octyl pyrrolidone | 19.70 | 20.94 |
| Stabaxol 1 (a) | 9.40 | 9.95 |
| Ethox CO-16 (b) | 35.40 | 37.70 |
| Tween 80 (C) | 29.50 | 31.41 |
| CaO | 6.00 | 0.00 |

(a) bis(di-isopropyl phenyl) carbodiimide
(b) 16 ethoxylated castor oil
(C) sorbitan monooleate ethoxylate Sample A, after 1 week storage at room temperature, contained 0.45 wt. % of residual water; whereas Sample B contained 1.07 wt. % H2O. When these samples were stored at 50° C., Sample A did not form a gel until 365 days; whereas Sample B gelled after 35 days.

When Sample B (100 g was stored at 50° C. over 1 part of CaO, the residual water content was reduced to 0.7%. The resulting sample, at 50° C. did not gel until after 100 days.

One week of storage at 50° C. is equivalent to more than six months storage at room temperature.

EXAMPLE 2

Biocidal concentrates were prepared by dissolving 7.4 g of Amitraz (87% pure) in 92.6 g of Samples A and B. After 2 weeks storage at 52° C., 99% of the original 7.4 g of Amitraz was retained in Sample A; however less than 95% of the original Amitraz was retained in Sample B.

EXAMPLE 3

The carrier concentrate for biocide in Sample B of Example 1 was prepared and dried to a water content to 0.5%. The sample was examined after 50 days storage at 50° C. and had completely gelled.

After the addition of 7.4 g Armitraz in 92.6 g of this sample and storage for 2 weeks at 52° C., less than 95% of the Amitraz remained in the sample.

EXAMPLE 4
Part A

Under a continuous blanket of nitrogen, 188.5 g of Ethox 16 and 157.05 g of Tween 80 were charged to a three-necked, round bottom flask equipped with a thermometer, a nitrogen inlet and a vacuum system. The water content of this mixture was 1.5%. The contents of the flask was heated and maintained at a temperature of 50–60° C. for 6 hours; after which the flow of nitrogen was discontinued and the flask was kept under vacuum at 2–3 mm Hg for an additional period of 3 hours. The water content was then analyzed to be less than 0.4%.
Part B A biocidal concentrate was prepared by dissolving a mixture of 40 g of Armitraz and 49.75 g of Stabaxol 1 in 104.7 g of N-octyl pyrrolidone and the resulting mixture added to Part A to produce 540 g of biocidal concentrate containing 6.44% Amitraz. After storage for 2 weeks at 52° C., the content of Amitraz was less than 95% of the original concentration.

The above biocidal concentrate was divided into 2 aliquot samples each 0.128 g aliquot sample was diluted with 40.0 g of water to provide 206 ppm concentration of Amitraz. The diluted samples were held in an oven at 50° C. and analyzed for Amitraz concentration. After for 7 days the samples retained less than 85% of the original amount of Amitraz.

EXAMPLE 5

The following concentrates were prepared by mixing the ingredients shown in the following table at room temperature until uniform mixtures were obtained.

TABLE

| | wt. % | | | | |
|---|---|---|---|---|---|
| Ingredients | Sample C | Sample D | Sample E | Sample F | Sample G |
| Agsol Ex 8 | 18.1 | 18.0 | 18.1 | 19.5 | 19.5 |
| Stabaxol 1 | 4.0 | 5.0 | 6.0 | 5.0 | 6.0 |
| Amitraz 87% | 7.4 | 7.4 | 7.4 | 7.4 | 7.4 |
| Ethox Co 16 | 32.5 | 32.5 | 32.5 | 34.6 | 34.6 |
| Tween 80 | 27.1 | 27.1 | 27.1 | 28.5 | 28.5 |
| Drapex 6.8 ESO* | 11.0 | 10.0 | 9.0 | 5.0 | 4.0 |

*Epoxidized vegetable oil

Samples C–G were stored in an oven at 50° C. and were free of gellation for 100 days. Stored samples C, D, F and G retained greater than 95% of the original Amitraz concentration; Sample E retained more than 98% Amitraz.

0.128 g samples C–G were diluted with 40.0 g of water to produce an Amitraz concentration of 206 ppm and stored in an oven at 50° C. and were found to retain more than 86% Amitraz after one week and Sample E showed only a 5% loss within this period.

It will be understood that many modifications and substitutions can be made in the above examples to achieve the present anti-gelling concentrates without departing from the scope of this invention. For example, other aza biocides disclosed herein can be substituted for AMITRAZ as well as other substitutions in the emulsifier mixture to achieve an HLB of 6–20, preferably 7–11.

What is claimed is:

1. A gel resistant, biocidally active concentrate or solution containing (a) between about 0.05 and about 25 wt. % of a biocidally active component; (b) between about 0 and about 40 wt. % of an organic oil; (c) between about 2 and about 20 wt. % of a terminally hindered carbodiimide; (d) between about 10 and about 80 wt. % of a lipophilic|hydrophilic emulsifier mixture having a HLB of from about 6 to 20 and (e) between about 0.5 and about 20 wt. %, based on (a) through (d), of an aliphatic anti-gelling agent selected from the group consisting of an inorganic oxide, an epoxidized ester of a naturally occurring or synthetic vegetable oil and an epoxidized ester of a saturated or unsaturated $C_6$ to $C_{18}$ aliphatic acid optionally containing hydroxy substitution and mixtures of said anti-gelling agents.

2. The gel-resistant biocidally active concentrate or solution of claim 1 in which said anti-gelling agent is an epoxidized compound wherein the epoxy moiety represents at least 5% of the total double bond and/or hydroxy content in the anti-gelling agent compound.

3. The composition of claim 1 wherein said carbodiimide contains a terminal nitrogen atom substituted with a radical selected from the group consisting of a lower alkyl phenyl, sulfonate, sulfonamide, imido, imidoester.

4. The composition of claim 1 wherein said carbodiimide is bis(tetra-and/or di-isopropyl phenyl) carbodiimide.

5. The composition of claim 1 wherein said carbodiimide is bis(alkoxyphenyl)carbodimide.

6. The composition of claim 1 wherein said emulsifier mixture has an acid number less than 5.

7. The composition of claim 6 wherein said emulsifier mixture includes an oil containing 5 to 60 $C_2$ to $C_3$ alkoxy groups.

8. The composition of claim 1 wherein said emulsifier mixture includes an ethoxylated castor oil.

9. The composition of claim 1 wherein said hydrophilic emulsifier is a hydroxylated ester of a carboxylic acid which contains 5 to 60 $C_2$ to $C_3$ alkoxy units or a mixture thereof.

10. The composition of claim 1 wherein said hydrophilic emulsifier is selected from the group consisting of an ethoxylated sorbitan mono-, di- and/or tri-oleate and a $C_8$ to $C_{12}$ alkyl phosphate or a mixture thereof.

11. The composition of claim 1 wherein said anti-gelling agent is employed at a concentration of between about 1 and about 15 wt. % of components (a) through (d) of the concentrate composition.

12. The composition of claim 1 wherein said anti-gelling agent is an oxide of Ca, Mg, Zn or Al or a mixture thereof.

13. The composition of claim 12 wherein said anti-gelling agent is $Al_2O_3$.

14. The composition of claim 1 wherein said anti-gelling agent is selected from the group consisting of epoxylated linseed, safflower or soybean oil or a mixture thereof.

15. The composition of claim 1 wherein said anti-gelling agent is epoxidized linseed oil.

16. The composition of claim 1 wherein the HLB of the emulsifier mixture is between 6 and 11.

17. The concentrate of claim 1 wherein the biocidal composition is water insoluble and the composition contains between about 5 and about 40 wt. % of a N—$C_8$ to $C_{12}$ alkyl pyrrolidone oil mixture.

18. The concentrate of claim 1 wherein the anti-gelling agent is a mixture containing at least two of the components selected from the group consisting of Ca oxide, epoxidized soybean oil and sorbitol.

19. The concentrate of claim 1 wherein the anti-gelling agent is a mixture of Ca oxide and epoxidized linseed oil or soybeean oil.

* * * * *